US00PP31483P2

(12) United States Plant Patent
Hansen

(10) Patent No.: US PP31,483 P2
(45) Date of Patent: Feb. 25, 2020

(54) ***PHLOX* PLANT NAMED 'BEDAZZLED ORCHID'**

(50) Latin Name: *Phlox hybrid*
Varietal Denomination: Bedazzled Orchid

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,920

(22) Filed: Feb. 1, 2019

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
See application file for complete search history.

*Primary Examiner* — Susan McCormick Ewoldt

(57) ABSTRACT

A unique cultivar of Hybrid Spring *Phlox* plant named *Phlox* 'Bedazzled Orchid' multi-stemmed compact habit, winter-hardy, slowly spreading plant with bright, glossy-green, lanceolate leaves. Flowers are sweetly fragrant, beginning in mid-April and continuing for about six weeks on branched peduncles. Petals are lavender-pink upon anthesis and lighten slightly with maturity. Petal apices are moderately notched and each blade has two deep purple striae marks near the center eye. Foliage stays clean and resists mildew, and the new plant is especially suitable for the landscape as a potted plant, in the garden as a specimen or en masse.

1 Drawing Sheet

Botanical classification: *Phlox* hybrid.
Variety denomination: 'Bedazzled Orchid'.

STATEMENT REGARDING PRIOR DISCLOSURES UNDER 37 CFR 1.77(B)(6)

The first public disclosure of the claimed plant, in the form of a photograph and brief description on a website operated by Walters Gardens, Inc. on Feb. 1, 2018. The claimed plant was first sold on Jul. 9, 2018 by Walters Gardens, Inc., who obtained the plant and all information relating thereto, from the inventor. No plants of *Phlox* 'Bedazzled Orchid' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Phlox* plant, known as *Phlox* 'Bedazzled Orchid' and will be referred to hereafter by its cultivar name, 'Bedazzled Orchid', or the "new plant". The new plant was hybridized by the inventor at a wholesale perennial nursery in Zeeland, Mich. on Mar. 3, 2014 as cross between *Phlox subulata* 'Emerald Pink' (not patented) as the female parent times *Phlox bifida* 'Top Notch' (not patented) as the male parent. The new plant passed initial evaluation in the spring of 2016 and was assigned the breeder code 14-240-8 through the remaining evaluation process. 'Bedazzled Orchid' was first asexually propagated by stem cuttings in the greenhouses at the same nursery in Zeeland, Mich. in the summer of 2016. The unique characteristics of the new plant have been found to be reproducible and stable in successive generations of asexual propagation and the resultant plants have been found to be identical to the original selection.

BRIEF SUMMARY OF THE PLANT

*Phlox* 'Bedazzled Orchid' is unique from all other Hybrid Spring *Phlox* or other *Phlox* known to the inventor. The nearest comparison plants known to the inventor include: 'Running with Scissors' U.S. Plant Pat. No. 28,738, 'Violet Pinwheels' U.S. Plant Pat. No. 25,884, 'Pink Parasol' U.S. Plant Pat. No. 28,881 and the two copending cultivars 'Bedazzled Lavender' U.S. Plant Pat. No. 31,168 and 'Bedazzled Pink' U.S. Plant patent application Ser. No. 16/350,913. 'Running with Scissors' has a flower color that is medium to light violet pink. 'Violet Pinwheels' has flowers that are violet-purple, and the flowering period is shorter with less coverage at peak flowering and the habit is more open. 'Pink Parasol' has a lighter pink flower with a white eye from anthesis to flower drop, and the two purple striae are thin and indistinct. 'Bedazzled Lavender' is slightly smaller in habit and the flower is lavender-pink, and the petals have a deeper apical notch and a more subtle purple eye. 'Bedazzled Pink' has flowers of bright medium pink and a star-shaped eye of dark purple. The female parent, 'Emerald Pink' is shorter in height, has a more rampant habit, foliage is shorter and awl-shaped, flowers of medium pink, and the petal lobes are rounded and not bifid. The male parent, *Phlox bifida* 'Top Notch' has pale lavender flower color with deeply cleft bifid petal lobes. The foliage of 'Bedazzled Orchid' are intermediate in size to the two parents.

*Phlox* 'Bedazzled Orchid' differs from and all other *phlox* known to the inventor in the following repeatedly observed traits in combination:

1. Plants of compact habit, slowly spreading by rooting of the stems, producing clean, glossy, bright-green, lanceolate leaves.
2. Multiple heavily-branched stems produce lightly branched panicles.
3. Flower beginning in mid-April and continuing for about six weeks completely covering plant at peak flowering.
4. Sweetly fragrant flowers with petals that begin lavender-pink and slightly lighten in maturity.
5. Individual petals are moderately notched at tips with two deep purple striae marks near the center eye.

BRIEF DESCRIPTION OF THE DRAWINGS

The photographs of the new plant demonstrate the unique traits of *Phlox* 'Bedazzled Orchid' and the overall appearance of the plant at three-years old growing in a full-sun trial bed in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
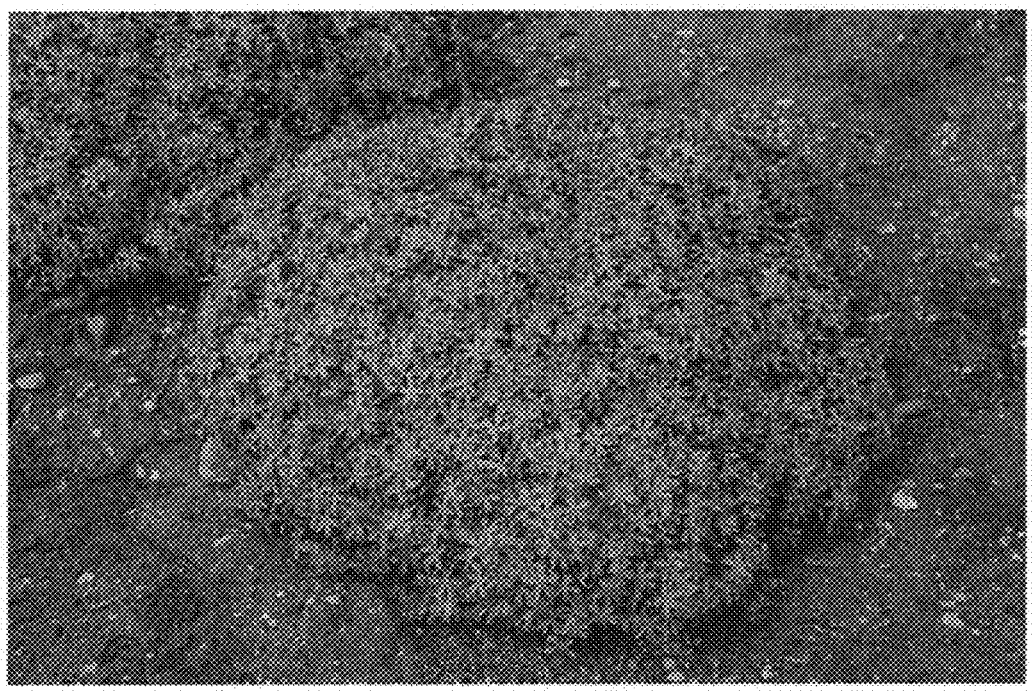
FIG. 1 shows the new plant in peak flower in the landscape in early May.
Figure 2:
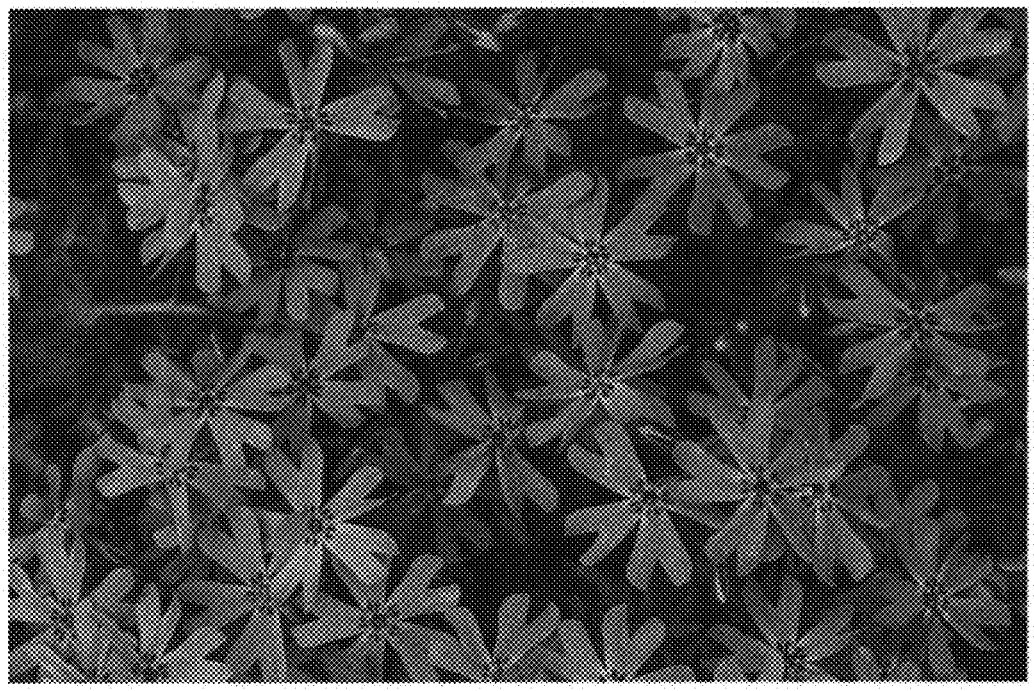
FIG. 2 shows a close-up of the flowers and buds.

The following descriptions and color references are based on the 2015 edition of The Royal Horticultural Society Colour Chart except where common dictionary terms are used. *Phlox* 'Bedazzled Orchid' has not been observed under all possible environments. The phenotype may vary slightly with different growing environments such as temperature, light, fertility, soil pH, moisture and maturity levels, but without any change in the genotype. The following observations and size descriptions are based on three-year-old plants in the full-sun trial garden of a wholesale perennial nursery in Zeeland, Mich. with supplemental fertilizer and water as needed.

Botanical classification: *Phlox* hybrid;

Parentage: Female or seed parent is *Phlox subulata* 'Emerald Pink', male or pollen parent is *Phlox bifida* 'Top Notch';

Plant habit: Winter-hardy herbaceous perennial; compact, highly branched; producing about 30 to 42 stiff, highly-branched stems; foliage 18.0 cm tall and 60.0 cm wide; flowering to 20.0 cm wide and 65.0 cm wide;

Propagation: Stem cuttings; rooting in about 10 days;

Time to produce finished crop in 3.8 liter pots: About 8 to 10 weeks; moderately vigorous;

Root: Fibrous and freely branching; color creamy white to tan depending on soil type;

Leaves: Simple; opposite; lanceolate, subulate; apex acute; base truncate, clasping; margin entire with basal one-quarter to whole margin micro-ciliolate; lustrous and glabrous both adaxial and abaxial; about 29.0 mm long by about 3.5 mm wide;

Leaf color: Adaxial nearest RHS 137A, abaxial nearest RHS 137B, base nearest RHS 157C;

Foliage fragrance: None detected;

Veins: Pinnate; not conspicuous adaxial and abaxial;

Vein color: Same color as surround leaf;

Petiole: Leaves sessile;

Stems: Cylindrical; stiff; strong; upright; covered in leaves distally; about 16.0 mm long and 3.0 mm diameter at base;

Stem color: Variable, nearest RHS 199C and RHS 146D in exposed proximal region;

Nodes: Proximally about 12.0 mm apart; distally less than 1.0 mm apart;

Node color: Same as surrounding stem;

Flowers: Perfect; salverform; cupped; about 22.0 mm across the flat face; with fused corolla tube about 15.0 mm long and 2.0 mm diameter; in branched panicle of about 3 to 4 flowers; attitude upright to outwardly;

Flower longevity: About 5 days on plant; self-cleaning;

Flower fragrance: Pleasantly sweet;

Buds one to two days prior to opening: Narrowly oblanceolate, to narrowly clavate; acute apex with petals implicate; about 21.0 mm long and 2.0 mm diameter in tube and 3.5 mm diameter toward apex;

Bud color: Nearest RHS N88C distally with center portion nearest blend of RHS 85D and lighter than RHS 160D and calyx tube nearest RHS 79A;

Petals: Five; glabrous; cleft blade and fused claw; blades not imbricate; apex bifid to about 4.0 mm deep and lobes separated about 3.0 mm at apex; blade about 9.0 mm long and 3.0 mm wide before tube; blade about 7.0 mm across at widest point near apex; base fused into a tube about 15.0 mm long and 2.0 mm diameter;

Petal color: Adaxial blade: main blade opening nearest between RHS N82B and lightening in maturity to between RHS 84C and RHS 84D with 2.0 mm central eye opening nearest RHS N82B with each petal having two spots about 1.0 mm long between RHS 93A and RHS 93B; central eye lightening to nearest RHS 76C in maturity; Abaxial blade: nearest RHS N82D;

Inner corolla tube: Nearest RHS 82D, basal 2.0 mm nearest RHS 145C;

Outer corolla tube: Nearest RHS 85A and lightening to lighter than RHS 145D at base;

Androecium:

*Filaments*.—Usually five, adnate to inner corolla at various heights; about 1.0 mm and 0.1 mm in diameter; color nearest RHS NN155D.

*Anther*.—Oblong elliptic; dorsifixed; oblong, about 2.0 mm long by 0.7 mm wide; color nearest RHS 17B.

*Pollen*.—Nearly microscopic, spherical; color nearest RHS 23A.

Gynoecium: One pistil per flower; 13.0 mm long;

*Style*.—Cylindrical; about 11.0 mm long and 0.2 mm diameter when flower is mature; color nearest RHS 157D.

*Stigma*.—Trifid in proximal 1.0 mm, about 0.2 mm diameter; persistent after flower abscission; nearest RHS 1C.

*Ovary*.—Inferior; globose; about 1.0 mm long and 1.0 mm diameter; color nearest RHS 144A.

Calyx: Campanulate; about 9.0 mm long and 3.5 mm across at apex;

Sepals: Five; linear; glabrous; acute apex, fused in basal 4.0 mm; margin entire, ciliate; pubescent abaxial, glabrous and lustrous adaxial; individually about 9.0 mm long and 1.0 mm wide at fusion;

Sepal color: Adaxial nearest RHS 137B and abaxial nearest RHS 137C with a blush of nearest RHS N77A;

Peduncle: Finely puberulent; strong, flexible; upright, cylindrical; about 1.5 mm diameter at base and 3.4 cm long;

Peduncle color: Nearest RHS N77A;

Pedicle: Cylindrical; finely puberulent; flexible; upright to outwardly; to about 10.0 mm long and 1.0 mm diameter;

Pedicle color: RHS N77A;

Fruit and seeds: Not yet been observed;

Hardiness and culture: The new plant grows best with full sun, plenty of moisture and adequate drainage, and can tolerate drier conditions once established; hardy to at least from USDA zone 4 through 8.

Disease and pest resistance: *Phlox* 'Bedazzled Orchid' demonstrates excellent powdery mildew resistance under conditions that would normally show symptoms. Further resistance or susceptibility beyond that of other Hybrid Spring *Phlox* is not known.

I claim:

1. A new and distinct cultivar of Hybrid Spring *Phlox* plant named *Phlox* 'Bedazzled Orchid', as herein described and illustrated.

* * * * *